US010247694B2

(12) United States Patent
Mishima et al.

(10) Patent No.: US 10,247,694 B2
(45) Date of Patent: Apr. 2, 2019

(54) GAS SENSOR CONTROL DEVICE

(71) Applicant: DENSO CORPORATION, Kariya, Aichi-pref. (JP)

(72) Inventors: Takao Mishima, Kariya (JP); Shingo Nakata, Kariya (JP); Mikiyasu Matsuoka, Kariya (JP); Tomoo Kawase, Kariya (JP); Yuuji Yamada, Kariya (JP)

(73) Assignee: DENSO CORPORATION, Kariya (JP)

( * ) Notice: Subject to any disclaimer, the term of this patent is extended or adjusted under 35 U.S.C. 154(b) by 434 days.

(21) Appl. No.: 15/023,446

(22) PCT Filed: Sep. 25, 2014

(86) PCT No.: PCT/JP2014/004904
§ 371 (c)(1),
(2) Date: Mar. 21, 2016

(87) PCT Pub. No.: WO2015/045382
PCT Pub. Date: Apr. 2, 2015

(65) Prior Publication Data
US 2016/0209352 A1    Jul. 21, 2016

(30) Foreign Application Priority Data
Sep. 27, 2013   (JP) ................. 2013-202133

(51) Int. Cl.
*G01N 27/407* (2006.01)
*G01N 27/406* (2006.01)
(Continued)

(52) U.S. Cl.
CPC ..... *G01N 27/4065* (2013.01); *F02D 41/1456* (2013.01); *F02D 41/1494* (2013.01);
(Continued)

(58) Field of Classification Search
CPC .................................................. G01N 27/4065
See application file for complete search history.

(56) References Cited

U.S. PATENT DOCUMENTS 4,178,793 A * 12/1979 Bremer ............... F02D 41/1494
 123/688
4,359,030 A * 11/1982 Sone .................. F02D 41/1494
 123/697
(Continued)

FOREIGN PATENT DOCUMENTS

JP    62-76451    4/1987

OTHER PUBLICATIONS

International Search Report for PCT/JP2014/004904 dated Dec. 9, 2014, 5 pages.
Written Opinion of the ISA for PCT/JP2014/004904 dated Dec. 9, 2014, 9 pages.
Nakata et al., copending U.S. Appl. No. 15/023,435, filed Mar. 21, 2016.
(Continued)

*Primary Examiner* — Alexander S Noguerola
(74) *Attorney, Agent, or Firm* — Nixon & Vanderhye P.C.

(57) ABSTRACT

An $O_2$ sensor includes a sensor element using a solid electrolyte layer and a pair of electrodes placed at a position to interpose the solid electrolyte layer, detects an exhaust gas from an internal combustion engine as an object of a detection, and outputs an electromotive force signal depending on an air-fuel ratio of the exhaust gas. The sensor element is connected with a constant current circuit supplying a constant current that is prescribed. A microcomputer calculates an element resistance, determines whether the air-fuel ratio is at least rich, lean, or stoichiometric, on the basis of a comparison between an electromotive force output of the electrogenic cell and a prescribed threshold. Further, the microcomputer controls the constant current supplied by the constant current circuit on the basis of the element resistance.

5 Claims, 8 Drawing Sheets

(51) Int. Cl.
   *F02D 41/14*    (2006.01)
   *F02D 41/24*    (2006.01)
   *G01N 27/41*    (2006.01)
   *F02D 41/06*    (2006.01)
   *F02D 41/12*    (2006.01)

(52) U.S. Cl.
   CPC ..... *F02D 41/2432* (2013.01); *F02D 41/2474* (2013.01); *G01N 27/4067* (2013.01); *G01N 27/4071* (2013.01); *G01N 27/41* (2013.01); *F02D 41/064* (2013.01); *F02D 41/123* (2013.01)

(56) References Cited

U.S. PATENT DOCUMENTS

| | | | |
|---|---|---|---|
| 4,719,895 | A | 1/1988 | Mieno et al. |
| 5,340,462 | A * | 8/1994 | Suzuki ............... F02D 41/1481 123/688 |
| 2003/0005746 | A1 | 1/2003 | Iwazaki et al. |
| 2008/0277281 | A1 | 11/2008 | Hiraiwa et al. |
| 2012/0043205 | A1 | 2/2012 | Matsuoka et al. |
| 2013/0192211 | A1 | 8/2013 | Nakano et al. |
| 2013/0255232 | A1 | 10/2013 | Maeda |
| 2015/0025778 | A1 | 1/2015 | Matsuoka et al. |

OTHER PUBLICATIONS

Mishima et al., copending U.S. Appl. No. 15/023,441, filed Mar. 21, 2016.

* cited by examiner (a)

(b)

GAS SENSOR CONTROL DEVICE

CROSS REFERENCE TO RELATED APPLICATION

This application is the U.S. national phase of International Application No. PCT/JP2014/004904 filed on Sep. 25, 2014 which designated the U.S. and claims priority to Japanese Patent Application No. 2013-202133 filed on Sep. 27, 2013, the entire contents of each of which are hereby incorporated by reference.

TECHNICAL FIELD

The present disclosure relates to a gas sensor control device.

BACKGROUND ART

For example, a vehicle engine generally uses an electromotive force output type gas sensor which takes the exhaust gas discharged from the engine as an object of detection and detects the oxygen concentration. The gas sensor has an electrogenic cell which outputs an electromotive force signal which differs depending on whether the exhaust gas air-fuel ratio is rich or lean. Specifically, when the air-fuel ratio is rich, the gas sensor outputs an electromotive force signal of about 0.9 V and when the air-fuel ratio is lean, the gas sensor outputs an electromotive force signal of about 0 V.

As for this kind of gas sensor, attention has been drawn to the fact that when the air-fuel ratio of the exhaust gas changes to rich or lean, the sensor output changes with a delay from the actual change of the air-fuel ratio. Various techniques have been described to improve this output characteristic.

For example, in the gas sensor control device in Patent Literature 1, a constant current circuit is connected to at least one of a pair of sensor electrodes. When it is determined that a change request to change the output characteristic of the gas sensor has been generated, the direction of constant current is determined according to the change request and the constant current circuit is controlled so that the constant current flows in the determined direction. Thus, the output characteristic of the gas sensor is appropriately controlled by supplying the constant current.

In a gas sensor, the resistance value of the sensor element changes depending on the temperature of the sensor element. Specifically, when the engine is started in the cold or when the exhaust gas temperature decreases with fuel cut to the engine, the element resistance increases with the decrease in the temperature of the sensor element. In this case, as the element resistance increases, the voltage applied to the sensor element increases even under the condition that a constant current flows. Because of this, the accuracy of determination about a rich or lean air-fuel ratio may decrease. The sensor element corresponds to an electrogenic cell. The resistance value of the sensor element is also called the element resistance.

More specifically, in the microcomputer which receives electromotive force output from the gas sensor, a first threshold which is on a richer side than the stoichiometric value (0.45 V) and a second threshold which is on a leaner side than the stoichiometric value (0.45 V) are predetermined. For example, the first threshold is set to 0.6 V and the second threshold is set to 0.3 V. When the electromotive force output is larger than the first threshold, the air-fuel ratio is determined as rich and when the electromotive force output is smaller than the second threshold, the air-fuel ratio is determined as lean. In this case, when the voltage applied to the sensor increases due to an unintentional change in the element resistance, air-fuel ratios which are determined as rich (or lean) would vary widely, resulting in decrease in the accuracy of air-fuel ratio determination. This problem arises because the air fuel ratio is determined as rich or lean not in the region of the gas sensor output characteristic where the electromotive force output rapidly changes, but its stable region which is on a richer or leaner side than the rapid change region. Therefore, in ensuring the accuracy of air-fuel ratio determination, there is room for improvement.

PRIOR ART LITERATURES

Patent Literature

Patent Literature 1: JP2012-63345A

SUMMARY OF INVENTION

The present disclosure has an object to provide a gas sensor control device which can make an air-fuel ratio determination appropriately under a condition that a constant current is supplied to a gas sensor.

According to an aspect of the present disclosure, a gas sensor control device is applied to a gas sensor which has an electrogenic cell using a solid electrolyte body and a pair of electrodes placed at a position to interpose the solid electrolyte body, and detects an exhaust gas from an internal combustion engine as an object of a detection and outputs an electromotive force signal depending on an air-fuel ratio of the exhaust gas The gas sensor control device includes a constant current supplying section supplying a constant current that is prescribed to the electrogenic cell, a resistance value calculating section calculating a resistance value of the electrogenic cell, an air-fuel ratio determining section determining whether the air-fuel ratio is at least rich, lean, or stoichiometric, on the basis of a comparison between an electromotive force output of the electrogenic cell and a prescribed threshold, and a current control section controlling the constant current supplied by the constant current supplying section, on the basis of the resistance value of the electrogenic cell calculated by the resistance value calculating section.

While a constant current is supplied to an electrogenic cell, the output characteristic of the electrogenic cell shifts to either the rich side or lean side. At this time, in connection with the electromotive force of the sensor element, a voltage change equivalent to "element resistance (resistance value of the electrogenic cell)×constant current" occurs and when the output characteristic shifts to the rich side, a voltage change equivalent to "element resistance×constant current" occurs on the negative side or when the output characteristic shifts to the lean side, a voltage change equivalent to "element resistance×constant current" occurs on the positive side. In such case, the amount of voltage change to become larger than expected when due to an unintentional change in the element resistance, the accuracy of air-fuel ratio determination decreases.

According to the above configuration, since the constant current supplied to the electrogenic cell is controlled according to the resistance value of the electrogenic cell, the disadvantage that the accuracy of air-fuel ratio determination decreases unintentionally can be suppressed. In other words, the increase in the amount of change in the sensor applied voltage due to increase in the resistance value of the electrogenic cell can be suppressed by decreasing the constant current. Thus, the decrease in the accuracy of air-fuel ratio determination can be suppressed. Consequently, air-fuel ratio determination can be made appropriately while the constant current is supplied to the gas sensor.

BRIEF DESCRIPTION OF DRAWINGS

The above and other objects, features and advantages of the present disclosure will become more apparent from the following detailed description made with reference to the accompanying drawings. In the drawings.

DESCRIPTION OF EMBODIMENTS

Figure 1:
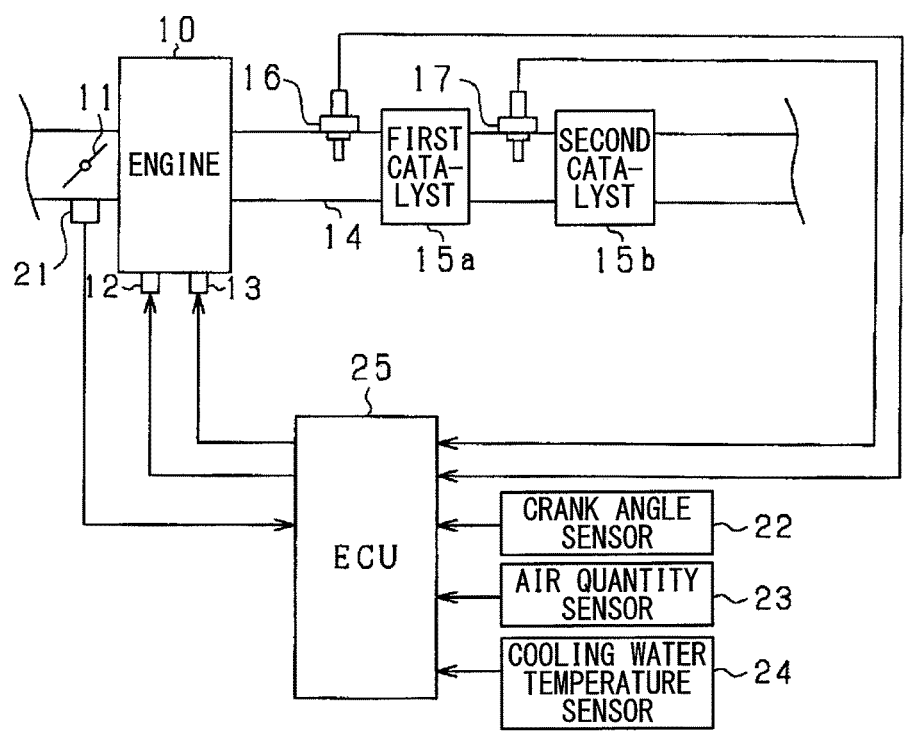
FIG. 1 is a schematic diagram which shows the general configuration of an engine control system.

Next, an embodiment of a gas sensor control device according to the present disclosure will be described referring to drawings. This embodiment concerns an engine control system which uses a gas sensor located on the exhaust pipe of an on-vehicle engine (internal combustion engine) to perform various controls, etc. of the engine according to output of the gas sensor. The control system, centered on an electronic control unit (ECU), performs control of the amount of fuel injection, control of ignition timing and so on. FIG. 1 is a block diagram which shows the general configuration of the system.

In FIG. 1, an engine 10 is, for example, a gasoline engine which includes a throttle valve 11 that is electronically controlled, a fuel injection valve 12, and an ignition device 13. An exhaust pipe 14 of the engine 10 is provided with catalysts 15a and 15b as exhaust gas purifying devices. The exhaust pipe 14 corresponds to an exhaust section. The catalysts 15a and 15b are, for example, both three-way catalysts; the catalyst 15a is a first catalyst as an upstream catalyst and the catalyst 15b is a second catalyst as a downstream catalyst. As widely known, a three-way catalyst purifies three major emission toxic components, carbon monoxide (CO), hydrocarbon (HC), and nitrogen oxide (NOx) such as NO, and is structured so that metal such as platinum, palladium, or rhodium is supported by a honeycomb or lattice-shaped ceramic support. In this case, the three-way catalyst purifies CO and HC as rich components by oxidation action and NOx as a lean component by reduction action.

An A/F sensor 16 is located upstream of the first catalyst 15a and an $O_2$ sensor 17 is located between the catalysts 15a and 15b (downstream of the first catalyst 15a and upstream of the second catalyst 15b). The A/F sensor 16 outputs an A/F signal which is roughly proportional to the air-fuel ratio of the exhaust gas. The $O_2$ sensor 17 also outputs an electromotive force signal which differs depending on whether the air-fuel ratio of the exhaust gas is lean or rich.

The system further includes various sensors including a throttle opening sensor 21 which detects the opening of the throttle valve 11, a crank angle sensor 22 which outputs a rectangular crank angle signal at every prescribed crank angle of the engine, an air quantity sensor 23 which detects the quantity of intake air in the engine 10, and a cooling water temperature sensor 24 which detects the temperature of engine cooling water. In addition to the above, the system includes a combustion pressure sensor which detects the combustion pressure in the cylinder, an accelerator opening sensor which detects the opening of the accelerator (amount of operation of the accelerator), and an oil temperature sensor which detects the temperature of engine lubricant, though not shown in the figure. In this embodiment, the prescribed crank angle is 30° CA cycle. These sensors correspond to an operation condition detecting section.

An ECU 25 is mainly comprised of a known microcomputer 41 which includes a CPU, ROM, and RAM, and executes various control programs stored in the ROM to perform various controls of the engine 10 depending on each engine operation condition. In other words, the ECU 25 receives signals from the above various sensors, etc. and calculates the amount of fuel injection and ignition timing according to the various signals to control the drive of the fuel injection valve 12 and the ignition device 13.

In connection with the amount control of fuel injection, the ECU 25 performs air-fuel ratio feedback control according to a detection signal from the A/F sensor 16 on the upstream of the first catalyst and a detection signal from the $O_2$ sensor 17 on the downstream of the first catalyst. Specifically, the ECU 25 performs main feedback control so that the actual air-fuel ratio (actual air-fuel ratio on the catalyst upstream side) detected by the A/F sensor 16 becomes a target air-fuel ratio set according to the engine operation condition, and also performs sub-feedback control so that the actual air-fuel ratio (actual air-fuel ratio on the catalyst downstream side) detected by the $O_2$ sensor 17 becomes the target air-fuel ratio. In sub-feedback control, for example, according to the difference between the actual air-fuel ratio on the catalyst downstream side and the target air-fuel ratio, the target air fuel ratio in main feedback control is modified or the amount of feedback correction in the main feedback control is modified. For air-fuel ratio control, for example, the ECU 25 performs stoichiometric feedback to make the target air-fuel ratio stoichiometric or nearly stoichiometric. In this case, stoichiometry is equivalent to a theoretical air-fuel ratio.

Figure 2:
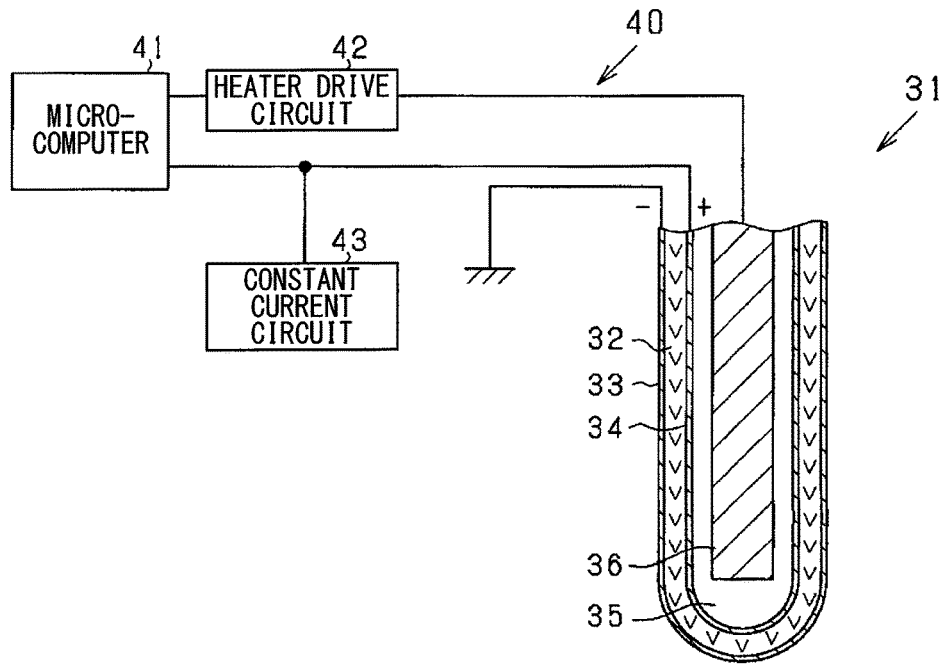
FIG. 2 is a diagram which shows the cross-sectional structure of a sensor element and the general structure of a sensor control section.

Next, the structure of the $O_2$ sensor 17 on the downstream of the first catalyst will be described. The $O_2$ sensor 17 has a sensor element 31 with a cup-shaped structure. FIG. 2 shows the cross-sectional structure of the sensor element 31. Specifically, the sensor element 31 has a roughly U-shaped cross section. Actually, the sensor element 31 is entirely housed in a housing or element cover and installed in the engine exhaust pipe. The sensor element 31 corresponds to an electrogenic cell.

The sensor element 31 has a solid electrolyte layer 32 with a roughly U-shaped cross section and an exhaust side electrode 33 on its outer surface and an air side electrode 34 on its inner surface. These electrodes 33 and 34 lie as layers on the surfaces of the solid electrolyte layer 32. The solid electrolyte layer 32 has an oxygen ion-conductive sintered oxide made by dissolving CaO, MgO, Y2O3, Yb2O3 or the like as a stabilizer in $ZrO_2$, $HfO_2$, $ThO_2$, Bi2O3 or the like. The electrodes 33 and 34 are both made of a catalytically active precious metal such as platinum and have a porous chemical coating or the like on their surfaces. The electrodes 33 and 34 are a pair of opposite electrodes and also called sensor electrodes. The inner space surrounded by the solid electrolyte layer 32 is an air chamber 35, and a heater 36 is housed in the air chamber 35. The air chamber 35 is also called the reference chamber. The heater 36 has a sufficient heat generating capacity to activate the sensor element 31 and heats the entire sensor element with its generated heat energy. The activation temperature of the $O_2$ sensor 17 is, for example, about 500 to 650° C. The inside of the air chamber 35 is maintained at a prescribed oxygen concentration by introduction of the air.

In the above sensor element 31, the outer side of the solid electrolyte layer 32 which is near the exhaust side electrode 33 has an exhaust gas atmosphere and the inner side of the solid electrolyte layer 32 which is near the air side electrode 34 has an air atmosphere, and depending on the oxygen concentration difference (oxygen partial pressure difference) between them, an electromotive force is generated between the electrodes 33 and 34. In short, an electromotive force which differs depending on whether the air-fuel ratio is rich or lean is generated. In this case, the exhaust side electrode 33 is lower in oxygen concentration than the air side electrode 34 as the reference electrode and in the sensor element 31, an electromotive force is generated with the air side electrode 34 as the positive side and the exhaust side electrode 33 as the negative side. Consequently, the $O_2$ sensor 17 outputs an electromotive force signal which depends on the oxygen concentration of the exhaust gas (namely, air-fuel ratio).

Figure 3:
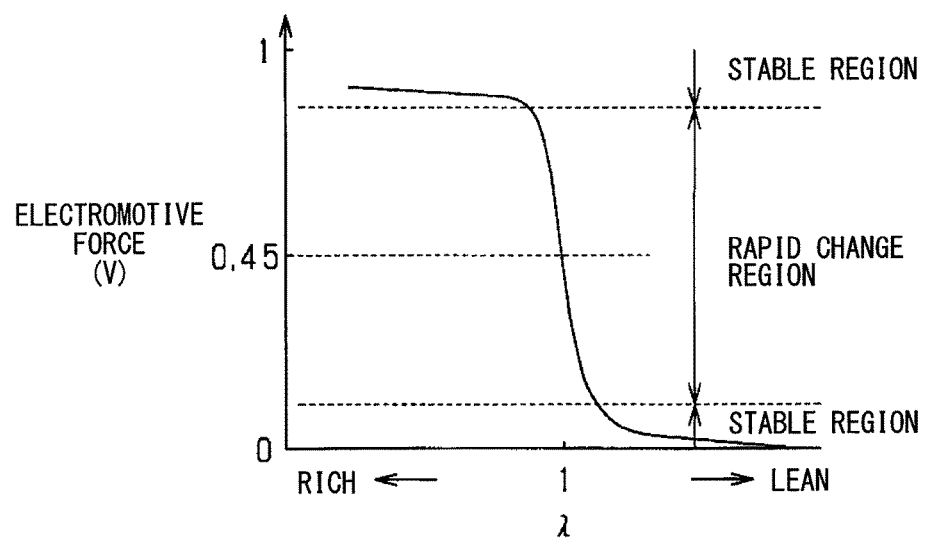
FIG. 3 is an electromotive force characteristic graph which shows the relation between excess air ratio and the electromotive force of the sensor element.

FIG. 3 is an electromotive force characteristic graph which shows the relation between excess air ratio $\lambda$ of the exhaust gas and the electromotive force of the sensor element 31. In FIG. 3, the horizontal axis represents excess air ratio $\lambda$ and when $\lambda$ is 1, the air-fuel ratio of the exhaust gas is stoichiometric. The sensor element 31 generates an electromotive force which differs depending on whether the air-fuel ratio is rich or lean, and has a characteristic that the electromotive force suddenly changes when the ratio is nearly stoichiometric. Specifically, when the ratio is rich, the electromotive force of the sensor element 31 is about 0.9 V and when the ratio is lean, the electromotive force of the sensor element 31 is about 0 V. As shown in FIG. 3, an electromotive force characteristic (an output characteristic of the $O_2$ sensor 17) includes a rapidly-changing voltage region where the electromotive force changes rapidly in the vicinity of the stoichiometric point, and stable voltage regions located on both sides of the rapidly-changing voltage region. In the stable voltage regions, the electromotive force is almost constant.

In FIG. 2, a sensor control section 40 is connected to the sensor element 31 and when an electromotive force is generated in the sensor element 31 depending on the air-fuel ratio (oxygen concentration) of the exhaust gas, a sensor detection signal (electromotive force signal) equivalent to the electromotive force is sent to a microcomputer 41 in the sensor control section 40. The microcomputer 41 calculates the air-fuel ratio according to the electromotive force signal from the sensor element 31. The sensor control section 40 is located in the ECU 25 shown in FIG. 1. In the ECU 25, the microcomputer 41 is provided as a calculating section which has an engine control function and a sensor control function. In this case, the microcomputer 41 calculates the engine rotation speed and the intake air amount according to the results of detection by the above various sensors. Alternatively, in the ECU 25, a microcomputer for engine control and a microcomputer for sensor control may be provided separately.

The microcomputer 41 makes a determination about the activity state of the sensor element 31 and also controls the heater 36 through a heater drive circuit 42 according to the result of the determination.

Furthermore, in this embodiment, in order to change the output characteristic of the $O_2$ sensor 17, a constant current that is prescribed is supplied between the pair of electrodes 33 and 34 in the sensor element 31. In this configuration, the sensor element 31 performs an oxygen pumping. The sensor element 31 increases the exhaust emission reduction effect in air-fuel ratio feedback control by changing the output characteristic. The principle on which the sensor output characteristic is changed by supplying a constant current is as follows.

Figure 4:
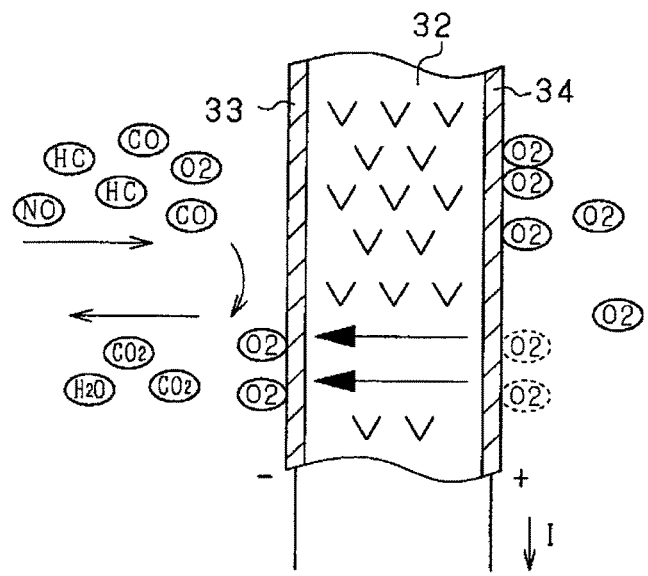
FIG. 4 is a schematic diagram which shows the reaction of gas components in the sensor element.
Figure 5:
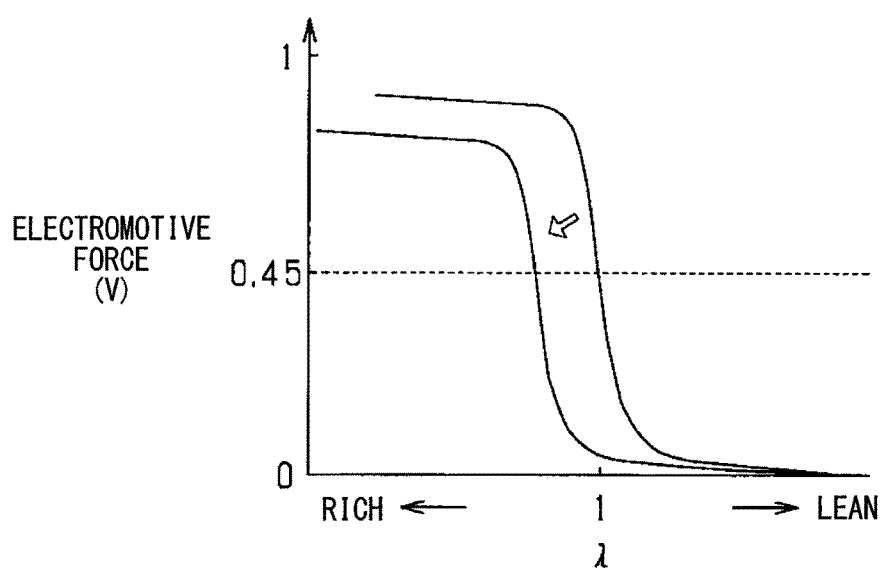
FIG. 5 is an electromotive force characteristic graph which shows the relation between excess air ratio and the electromotive force of the sensor element.

As shown in FIG. 4, there are CO, HC, NOx, and $O_2$ in the vicinity of the exhaust side electrode 33 of the $O_2$ sensor 17 and in this condition, a current is supplied to the sensor element 31 so that oxygen ions move from the air side electrode 34 to the exhaust side electrode 33 through the solid electrolyte layer 32. Specifically, oxygen pumping is performed in the sensor element 31. In this case, at the exhaust side electrode 33, the oxygens which have moved to the exhaust side electrode 33 through the solid electrolyte layer 32 react with CO and HC and generate $CO_2$ and H2O. Consequently, CO and HC are removed in the vicinity of the exhaust side electrode 33 and the equilibrium point of gas reaction in the vicinity of the exhaust side electrode 33 of the $O_2$ sensor 17 shifts to the rich side. In other words, as shown in FIG. 5, the sensor output characteristic which indicates the relation between excess air ratio $\lambda$ and electromotive force as a whole shifts to the rich side and accordingly, the point at which the electromotive force becomes the stoichiometric value (0.45 V) shifts to the rich side.

Next, the structure of the sensor control section 40 which performs control for the $O_2$ sensor 17 will be described. The structure of the sensor control section 40 is as illustrated in FIG. 2 and the sensor control section 40 has the microcomputer 41 as a control section. The microcomputer 41 receives an electromotive force signal from the sensor element 31 through an A/D converter, etc. and calculates the air-fuel ratio of the exhaust gas according to the electromotive force signal. Alternatively, the microcomputer 41 calculates the air-fuel ratio on the catalyst downstream according to the electromotive force signal. A constant current circuit 43 as a constant current supplying section is connected midway in an electric pathway which electrically connects the air side electrode 34 of the sensor element 31 and the microcomputer 41. When the sensor element 31 generates an electromotive force, the constant current circuit 43 receives the electromotive force from the sensor element 31 and supplies a current, which depends on the electromotive force, to the sensor element 31. In this case, according to the constant current circuit 43, the current flows from the exhaust side electrode 33 to the air side electrode 34 through the solid electrolyte layer 32 and accordingly oxygen ions move in the solid electrolyte layer 32 from the air side electrode 34 to the exhaust side electrode 33.

The structure of the constant current circuit 43 of the sensor control section 40 and the peripheral circuit around the circuit 43 will be described in more detail referring to FIG. 6.

Figure 6:
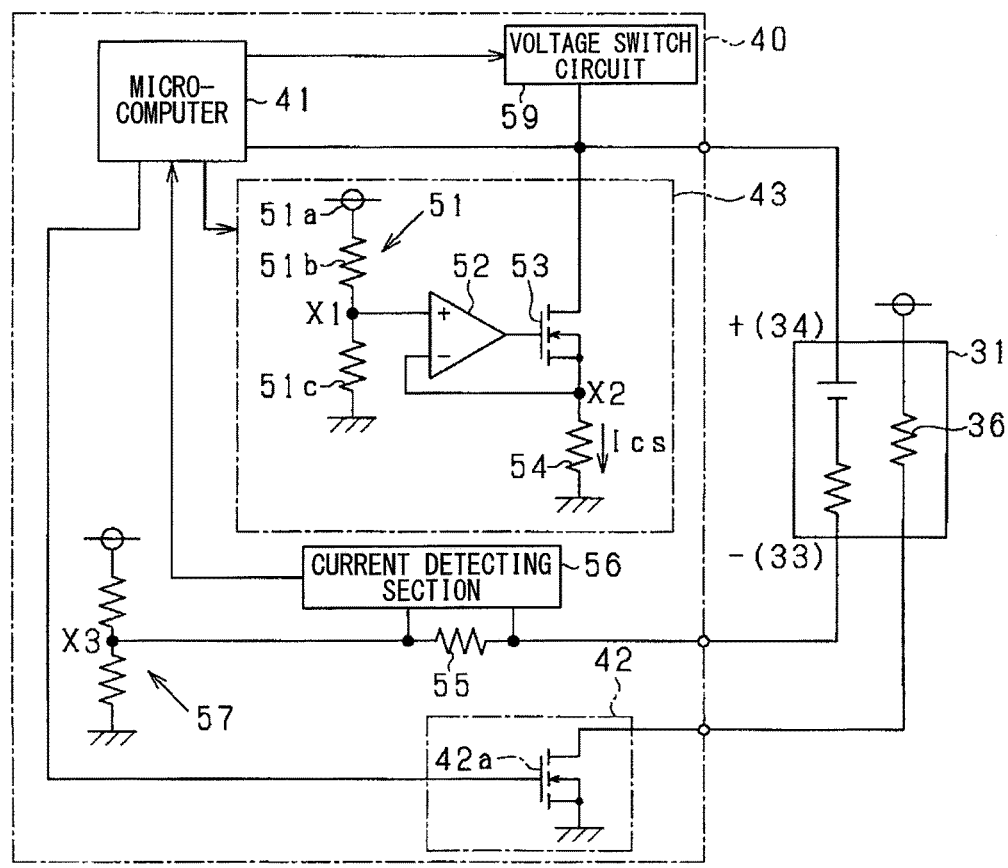
FIG. 6 is a diagram which shows the structure of the sensor control section.

In FIG. 6, the constant current circuit 43 includes a voltage generating section 51 to generate a prescribed constant voltage, an operational amplifier 52, an n-channel MOSFET 53 to be driven by output of the operational amplifier 52, and a resistance 54 connected to the source of the MOSFET 53. In the voltage generating section 51, a constant voltage source 51a and resistances 51b and 51c are connected in series and the middle point between the resistances 51b and 51c is voltage output point X1. In this embodiment, the constant voltage source 51a is 5 V. In the operational amplifier 52, the + input terminal is connected to voltage output point X1 and the output terminal is connected to the gate of the MOSFET 53. Also, the − input terminal is connected to middle point X2 between the MOSFET 53 and the resistance 54. From the viewpoint of the MOSFET 53, the gate is connected to the output terminal of the operational amplifier 52, the drain is connected to the air side electrode 34 of the sensor element 31 and the source is connected to the resistance 54.

The above constant current circuit 43 operates so that the voltage of the + input terminal of the operational amplifier 52 is equal to the voltage of its − input terminal, so the voltage at X2 becomes equal to the voltage at X1. Then, constant current Ics, the amount of which is determined by the voltage at X2 and the resistance value of the resistance 54, flows in the series circuit including the sensor element 31, MOSFET 53, and resistance 54. At this time, the MOSFET 53 operates according to the operational amplifier output voltage based on the difference between + and − input voltages and functions as a current control element which supplies a constant current Ics.

Here, the voltage at X1 and X2 and the resistance value of the resistance 54 should be determined according to the amount of current which is required to flow in the sensor element 31 when an electromotive force is generated in the sensor element 31. Specifically, when an electromotive force (0 to 0.9 V) is generated in the sensor element 31, when a current of 0.1 mA is to flow in the sensor element 31, for example, the voltage at X1 and X2 should be 10 mV and the resistance value of the resistance 54 should be 100Ω. When a current of 0.2 mA is to flow, for example, the voltage at X1 and X2 should be 20 mV and the resistance value of the resistance 54 should be 100Ω. When the current amount range is to be 0.1 to 2.0 mA, when the resistance value of the resistance 54 is 100Ω, the voltage at X1 and X2 should be in the rage of 10 mV to 200 mV.

In the sensor control section 40 which uses the above constant current circuit 43, when an electromotive force is generated in the sensor element 31, the prescribed constant current Ics flows in the MOSFET 53 and resistance 54 with the electromotive force as a power source (namely, the sensor element 31 functions as a battery). The output characteristic of the $O_2$ sensor 17 can be thus changed.

In this embodiment, the constant current Ics supplied by the constant current circuit 43 can be changed according to a command from the microcomputer 41 and the constant current Ics can be increased or decreased according to each condition. Specifically, the voltage value at points X1 and X2 are changed, for example, by changing the resistance ratio between the resistances 51b and 51c according to a command from the microcomputer 41 and accordingly the constant current Ics is changed.

The first end of a shunt resistance 55 for current detection is connected to the exhaust side electrode 33 of the sensor element 31 and the second end of the shunt resistance 55 is connected to a voltage circuit 57. The current which flows in the shunt resistance 55 is detected by a current detecting section 56 and the detection signals are sent to the microcomputer 41 sequentially. The current detecting section 56 may be a differential amplifier circuit which uses, for example, an operational amplifier or the like. In FIG. 2, in the sensor control section 40, components such as the shunt resistance 55 and voltage circuit 57 (other components than the constant current circuit 43 and heater drive circuit 42) are omitted.

The voltage circuit 57, which is intended to apply a positive voltage to the exhaust side electrode 33, is an offset voltage circuit which makes the potential of the exhaust side electrode 33 higher by a given potential than the potential on the side from which a current flows in the constant current circuit 43 (grounding side potential of the resistance 54). The voltage circuit 57 has a voltage dividing circuit which generates a prescribed offset voltage and the middle point of the voltage dividing circuit is offset voltage point X3. The voltage at the offset voltage point X3 is, for example, 2.0 V.

A voltage switch circuit 59 is connected to the air side electrode 34 of the sensor element 31. This voltage switch circuit 59 temporarily sweeps the voltage applied to the sensor element 31 according to a command from the microcomputer 41 and the resistance value of the sensor element 31 can be detected by the current detecting section 56 detecting the amount of current change with the voltage change. The resistance value of the sensor element 31 is also called the element resistance. The element resistance is detected in a given cycle and during the detection, the sensor applied voltage is changed by sweeping. When the applied voltage is changed by sweeping, the sensor applied voltage may be changed toward the positive side or toward both the positive and negative sides. In calculation of the element resistance, instead of changing the voltage by sweeping, the current may be changed by sweeping so that the element resistance is calculated from the amount of the resulting voltage change.

Furthermore, in the sensor control section 40, the heater drive circuit 42 has a switching element 42a which turns on/off the power to the heater 36. In the sensor element 31, heater energization is controlled by turning on/off the switching element 42a, so that the sensor element 31 is maintained in a prescribed active state. In this prescribed active state, the activation temperature is 500 to 650° C. The control of heater energization by the microcomputer 41 is briefly outlined below. Before activation of the sensor element 31, in order to expedite activation, the switching element 42a is kept ON and the heater 36 is heated with the maximum electric power. In this case, energization control is wholly performed. After activation of the sensor element 31, the amount of heater energization is feedback-controlled according to the difference between the target value and the actual value (calculated value) of the element resistance. For example, the amount of duty control at each time is calculated by the PID control method and energization of the heater is performed by turning on/off the switching element 42a according to the amount of duty control.

In air-fuel ratio control in this embodiment, determination is made at least as to whether the air-fuel ratio (the air-fuel ratio on the catalyst downstream) is rich, lean or stoichiometric, on the basis of comparison between the electromotive force output of the sensor element 31 and a prescribed threshold. Specifically, as thresholds to determine whether the air-fuel ratio is rich or lean, a first threshold V1 which is on a richer side than the stoichiometric value for the electromotive force of the sensor element 31 and a second threshold V2 which is on a leaner side than the stoichiometric value are determined and when the electromotive force output is larger than the first threshold V1, the microcomputer 41 determines that the air-fuel ratio is rich, or when the electromotive force output is smaller than the second threshold V2, the microcomputer 41 determines that the air-fuel ratio is lean. The first threshold V1 is, for example, 0.6 V and the second threshold V2 is, for example, 0.3 V. The microcomputer 41 controls the air-fuel ratio on the catalyst downstream so that the air-fuel ratio is within the near-stoichiometric range defined by these thresholds V1 and V2.

Figure 7:
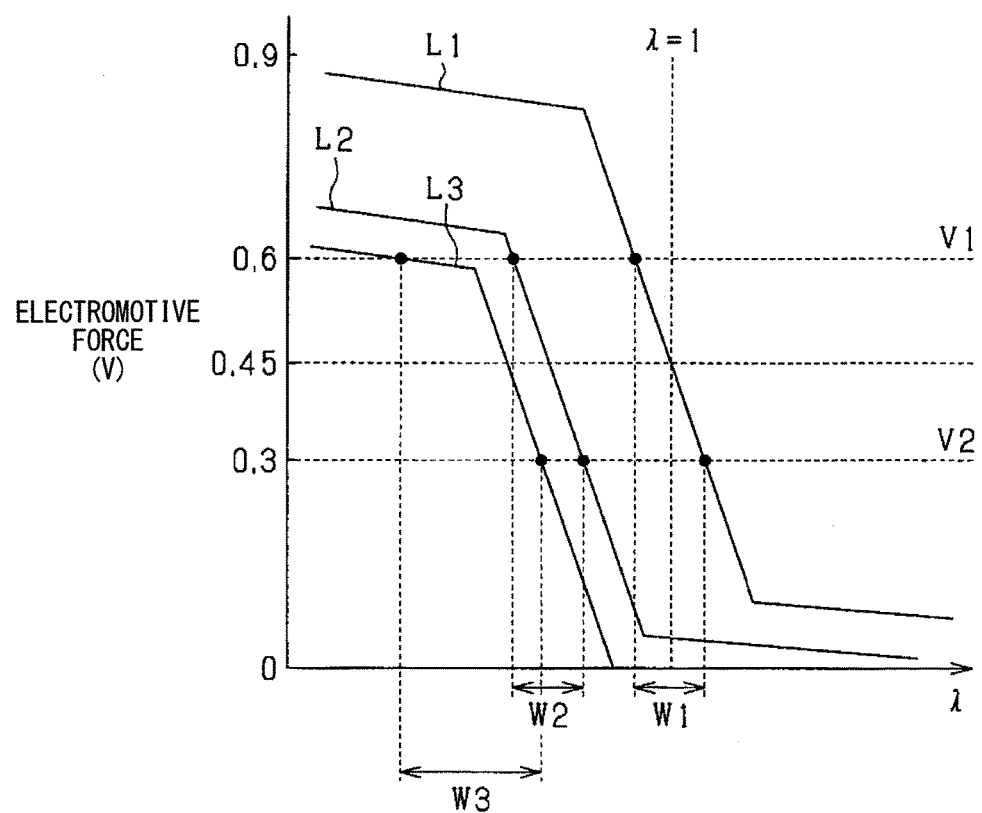
FIG. 7 is an electromotive force characteristic graph which shows the relation between electromotive force output and the supply of constant current.

Next, the relation between electromotive force output and the supply of constant current in the above air-fuel ratio determination will be described referring to FIG. 7. In FIG. 7, regarding the output characteristic of the $O_2$ sensor 17, L1 denotes an output characteristic without supply of constant current Ics and L2 and L3 denote output characteristics with supply of constant current Ics. Furthermore, when the temperature of the sensor element 31 is low during the cold start of the engine 10 or during fuel cut, the element resistance increases and the value of the electromotive force changes to a negative one due to the change in the sensor applied voltage with the increase in the element resistance. In addition to this point, regarding the output characteristics L2 and L3 with supply of constant current Ics, L2 indicates an output characteristic (ordinary characteristic) of the $O_2$ sensor 17 in which the resistance has not increased and L3 indicates an output characteristic of the $O_2$ sensor 17 in which the resistance has increased. For the convenience of explanation, output characteristic lines are indicated linearly in FIG. 7.

In output characteristic L2, a characteristic change equivalent to the constant current Ics and element resistance occurs as compared with output characteristic L1 (characteristic without current). In output characteristic L3, a characteristic change equivalent to an increase in the element resistance occurs as compared with output characteristic L2 (ordinary characteristic). The width of the near-stoichiometric range in which the thresholds V1 and V2 are used for determination is W1 for output characteristic L1, W2 for output characteristic L2, and W3 for output characteristic L3. In this case, whereas the width of the near-stoichiometric range for determination in output characteristic L2 is nearly equal to that in output characteristic L1 as the basic characteristic, the near-stoichiometric range for determination in output characteristic L3 is wider than in output characteristic L2 (so to speak, the range of variation is wider). L3 may be considered to indicate that due to an unintentional change in the element resistance, the amount of voltage change is larger than expected, and under such condition, the accuracy of air-fuel ratio determination is decreased. Since FIG. 7 shows a case that the output characteristic shifts to the rich side, the output characteristic has a voltage change in the negative direction; on the other hand, when the output characteristic shifts to the lean side, the voltage changes in the positive direction.

As mentioned above, the output characteristic of the $O_2$ sensor 17 may be said to have, near the stoichiometric point, a rapidly-changing voltage region where the electromotive force changes rapidly and, on both sides of that region, stable voltage regions where the electromotive force is almost constant (see FIG. 3). Whereas both rich/lean determinations are made in the rapidly-changing voltage region in output characteristics L1 and L2, in output characteristic L3 one of the rich/lean determinations is made in the rapidly-changing voltage region and the other determination is made in the stable voltage region.

When, while the constant current Ics is supplied to the sensor element 31 as mentioned above, the element resistance increases unintentionally as the temperature of the sensor element 31 becomes low, the air-fuel ratio determined as rich (or lean) varies widely and as a consequence the accuracy of air-fuel ratio determination decreases.

Therefore, in this embodiment, the element resistance Ra is calculated successively and the constant current Ics to be supplied to the sensor element 31 is controlled (corrected) according to the element resistance Ra, thereby suppressing the decrease in the accuracy of air-fuel ratio determination.

Figure 8:
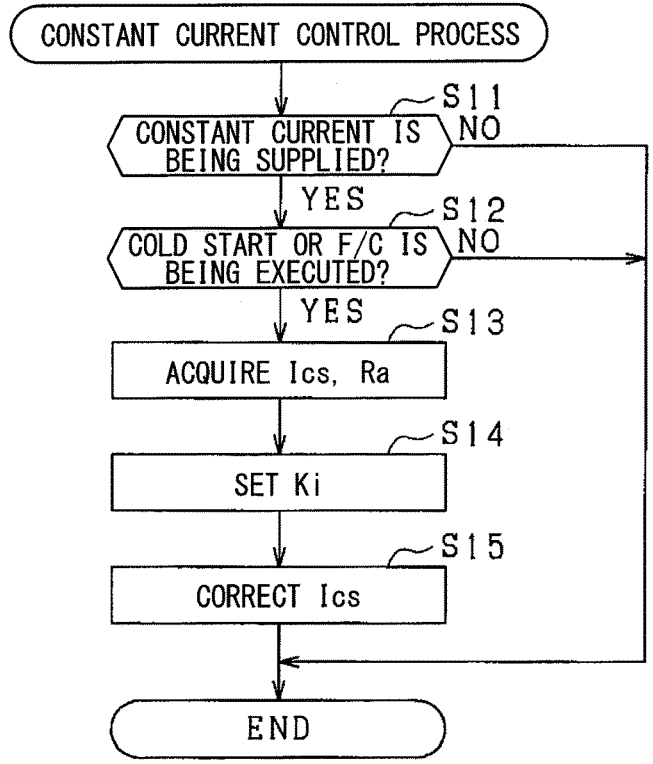
FIG. 8 is a flowchart which shows the constant current control process.

FIG. 8 is a flowchart which shows the constant current control process and this process is repeated by the microcomputer 41 in a given cycle.

In FIG. 8, at S11 the microcomputer 41 determines whether or not the constant current is now being supplied by the constant current circuit 43. At S12, the microcomputer 41 determines whether or not cold start of the engine 10 or fuel cut is being executed. In this embodiment, the step S12 corresponds to a low temperature determining section. When NO at S11 or S12, the microcomputer 41 ends this process or when YES at both S11 and S12, the microcomputer 41 proceeds to the next step S13.

At S13, the microcomputer 41 acquires the constant current Ics and element resistance Ra at a present time point. The constant current Ics may be switched to any one among a plurality of values (for example, 0.1 mA, 0.2 mA and so on). For example, the constant current Ics is set as a variable depending on the engine operation condition, etc. In short, when the engine operation condition changes, the amount of rich components in the exhaust gas changes accordingly. Specifically, when the engine rotation speed is higher or the engine load is larger, the amount of rich components in the exhaust gas increases. In this case, in order to maintain the desired performance concerning exhaust emissions, it is desirable to control the current to be supplied to the sensor element 31 (constant current Ics of the constant current circuit 43) as a variable depending on the engine operation condition. For example, when the engine rotation speed is higher or the engine load is larger, the constant current Ics is increased. In this embodiment, the step S13 corresponds to a constant current setting section.

Figure 9:
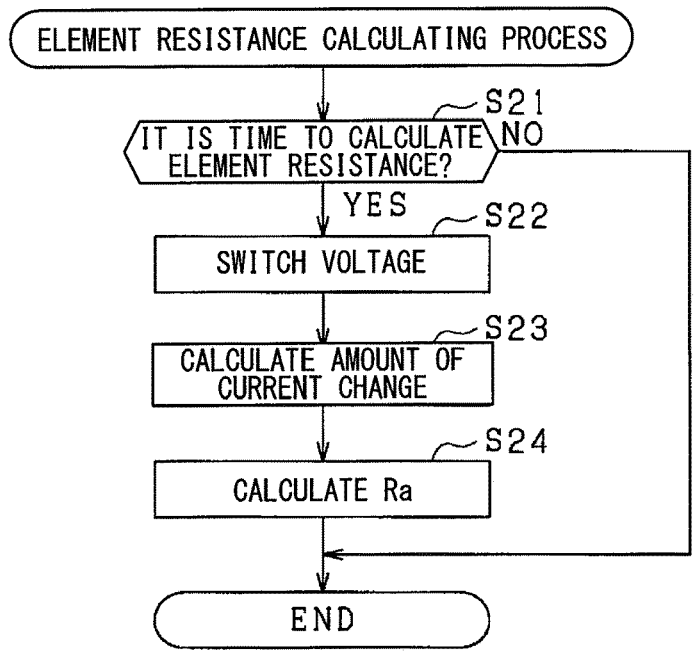
FIG. 9 is a flowchart which shows the element resistance calculating process.

The element resistance Ra should be calculated by the microcomputer 41 in a given cycle; for example, the element resistance Ra is calculated through the element resistance calculating process shown in FIG. 9. In FIG. 9, at S21 the microcomputer 41 determines whether or not it is time to calculate the element resistance. When the microcomputer 41 determines that it is time to calculate, the microcomputer 41 proceeds to S22. The element resistance calculation interval is, for example, 128 msec. At S22, the microcomputer 41 temporarily switches the sensor applied voltage through the voltage switch circuit 59. At S23, the microcomputer 41 calculates the amount of current change which occurs depending on the voltage change. Furthermore, at S24 the microcomputer 41 calculates the element resistance Ra from the amount of current change calculated at S23. In this embodiment, the step S24 corresponds to a resistance value calculating section.

Figure 10:
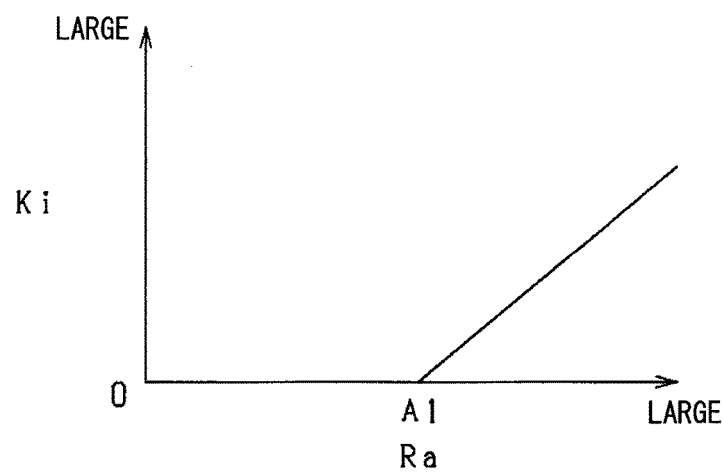
FIG. 10 is a graph which shows the relation between element resistance and current correction value.
Figure 10:
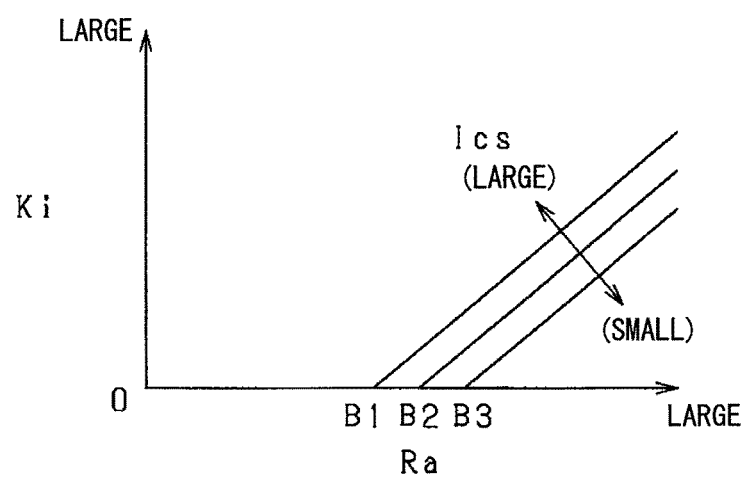

At S14, the microcomputer 41 sets a current correction value Ki to correct (decrease) the constant current Ics, according to the element resistance Ra. At this time, the current correction value Ki is set, for example, using the relation in FIG. 10 (a). According to FIG. 10 (a), when the element resistance Ra is A1 or more, the current correction value Ki is set to a larger value for a larger element resistance Ra. In other words, when the element resistance Ra is less than A1, the constant current Ics is not corrected (decreased) but when the element resistance Ra is A1 or more, the constant current Ics is corrected (decreased). A1 should be a target element resistance in heater energization control or a resistance value which is nearly equal to the target element resistance. In the arrangement that the constant current Ics is set as a variable, as shown in FIG. (b) the current correction value Ki should be set according to the element resistance Ra and constant current Ics. According to FIG. 10 (b), the element resistance Ra as the reference to determine whether to correct (decrease) the constant current Ics is set to a value which differs depending on the constant current Ics, namely B1, B2, or B3, and when the constant current Ics is larger, the element resistance Ra as the reference is smaller. As shown in FIG. 10 (b), B1 is smaller than B2 and B2 is smaller than B3. When the element resistance Ra is the same, the current correction value Ki is set to a larger value for a larger constant current Ics.

The control of constant current Ics should be performed so that in the sensor output characteristic having a rapidly-changing voltage region and a stable voltage region, the thresholds V1 and V2 remain included in the rapidly-changing voltage region. In other words, rich determination and lean determination are always made in the rapidly-changing voltage region of the sensor output characteristic. In this case, the set value of constant current Ics itself is determined within such a range that the thresholds V1 and V2 are included in the rapidly-changing voltage region, and the condition in which the thresholds V1 and V2 are included in the rapidly-changing voltage region can be maintained by performing current control so that a voltage change corresponding to Ics occurs.

After that, at S15 the microcomputer 41 corrects a present constant current Ics that is the constant current Ics at the present time point, by the current correction value Ki calculated at S14. In this embodiment, the steps S14 and S15 correspond to a current control section and also the step S14 corresponds to a correction value calculating section and the step S15 corresponds to a correction section. Specifically, as expressed by the formula (1) below, the corrected constant current Ics is the present constant current Ics minus the current correction value Ki. After the correction, the constant current Ics supplied by the constant current circuit 43 is controlled according to the corrected constant current Ics.

$$Ics = Ics - Ki \quad (1)$$

According to the embodiment detailed above, the following advantageous effects can be brought about.

Since the constant current Ics supplied to the sensor element 31 is controlled according to the element resistance Ra, the disadvantage that the accuracy of air-fuel ratio determination decreases unintentionally can be suppressed. In other words, the increase in the amount of change in the sensor applied voltage due to increase in the element resistance Ra can be suppressed by decreasing the constant current Ics. Thus, the decrease in the accuracy of air-fuel ratio determination can be suppressed. Consequently, air-fuel ratio determination can be made appropriately while the constant current Ics is supplied to the $O_2$ sensor 17.

One method of suppressing the increase in the amount of change in the sensor applied voltage other than by decreasing the constant current Ics is to decrease the element resistance by increasing the amount of heat generation by the heater 36. However, more electric power is required to increase the amount of heat generation by the heater 36, which is disadvantageous in terms of energy saving. In addition, when the element resistance is decreased by heating by the heater 36, a delay occurs from when heating is started until the temperature of the sensor element 31 actually increases, which may be undesirable from the viewpoint of response speed (element resistance restoration speed). Furthermore, an overshoot, etc. may occur when the element resistance changes, which may be undesirable from the viewpoint of controllability.

The current correction value Ki is calculated according to the element resistance Ra and the constant current Ics is corrected by the current correction value Ki (see FIG. 10 (a)). Therefore, even when the element resistance Ra changes unintentionally, the constant current Ics can be controlled appropriately in accordance with the change.

The current correction value Ki is calculated according to the element resistance Ra and constant current Ics (value set as a variable) and the constant current Ics is corrected by the current correction value Ki (see FIG. 10 (b)). In the arrangement that the constant current Ics is set as a variable, even when the element resistance Ra changes unintentionally, the constant current Ics can be controlled appropriately in accordance with the change.

The constant current is controlled so that in the electromotive force characteristic of the $O_2$ sensor 17 having a rapidly-changing voltage region and a stable voltage region, rich determination and lean determination are made in the rapidly-changing voltage region. Consequently, variance in rich determination and lean determination can be suppressed with certainty.

During the cold start of the engine 10 or during fuel cut, the temperature of the sensor element 31 is relatively low. At such a low temperature, wrong air-fuel ratio determination is likely to occur. In this respect, when it is determined that cold start or fuel cut is being executed, the above constant current control is performed, so a condition which is likely to cause a disadvantage can be addressed properly.

OTHER EMBODIMENTS

The above embodiment may be altered as follows.

(a) Under the condition that a constant current is supplied to the sensor element 31, when feedback control of the heater 36 is performed so as to control the element resistance Ra to be a target value Rtg, the constant current Ics may be changed when the element resistance Ra is different from the target value Rtg by a prescribed amount or more.

Figure 11:
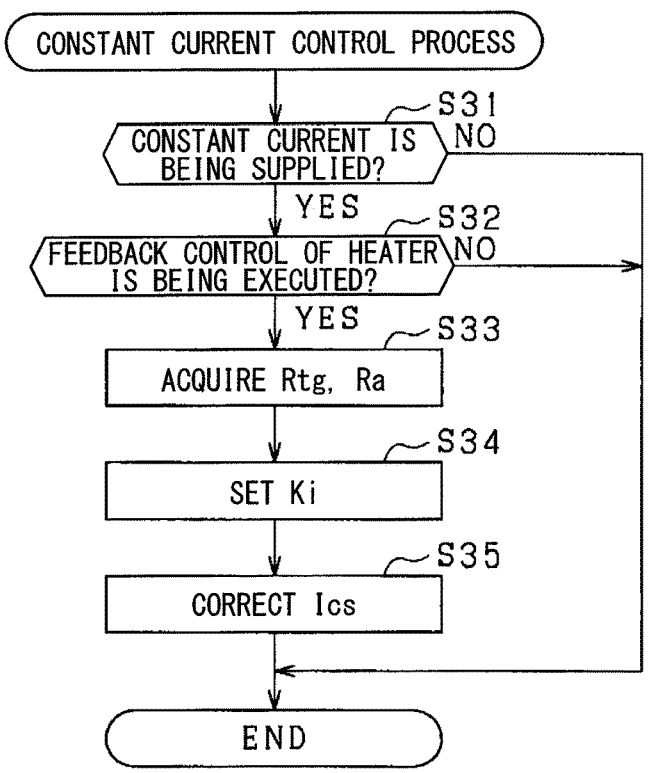
FIG. 11 is a flowchart which shows the constant current control process.

FIG. 11 is a flowchart which shows the constant current control process and this process is repeated by the microcomputer 41 in a given cycle. In FIG. 11, at S31 the microcomputer 41 determines whether or not the supply of constant current by the constant current circuit 43 is being executed. At S32, the microcomputer 41 determines whether or not feedback control of the heater 36 is being executed. In this embodiment, the step S32 corresponds to a heater control section. When NO at S31 or S32, the microcomputer 41 ends this process or when YES at both S31 and S32, the microcomputer 41 proceeds to the next step S33.

At S33, the microcomputer 41 acquires the target value Rtg and element resistance Ra. At S34, the microcomputer 41 sets a current correction value Ki to correct (decrease) the constant current Ics, according to deviation ΔR which is the difference between the target value Rtg and the element resistance Ra (=Ra−Rtg). At this time, the current correction value Ki is set using the relation in FIG. 12. The deviation ΔR is the element resistance Ra minus the target value Rtg as expressed by the formula (2) below.

$$\Delta R = Ra - Rtg \qquad (2)$$

Figure 12:
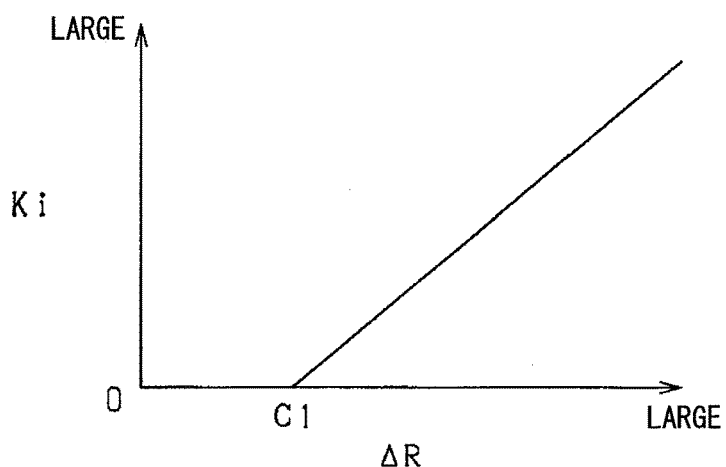
FIG. 12 is a graph which shows the relation between element resistance deviation and current correction value.

According to FIG. 12, when the element resistance deviation ΔR is C1 or larger, the current correction value Ki is set to a larger value for a larger deviation ΔR. In other words, when the deviation ΔR is smaller than C1, the constant current Ics is not corrected (decreased) but when the deviation ΔR is C1 or larger, the constant current Ics is corrected (decreased).

After that, at S35 the microcomputer 41 corrects the present constant current Ics by the current correction value Ki calculated at S34. In this embodiment, the steps S34 and S35 correspond to a current control section, the step S34 corresponds to a correction value calculating section and the step S35 corresponds to a correction section. Specifically the present constant current Ics is corrected in accordance with the above formula (1). After the correction, the constant current Ics supplied by the constant current circuit 43 is controlled according to the corrected constant current Ics.

According to the above arrangement, even when a deviation of the element resistance Ra from the target value Rtg occurs with a sudden change in the exhaust gas temperature, etc., air-fuel determination can be made appropriately.

(b) In the above embodiment, two thresholds V1 and V2 are used for the rich side and the lean side for the purpose of air-fuel ratio determination; however, instead of this, only one of them may be used. For example, only the first threshold V1 for the rich side may be used to determine whether or not the air-fuel ratio is rich.

(c) In the above embodiment, an example in which the present disclosure is applied to an $O_2$ sensor 17 with a heater has been explained; however, instead of this, the disclosure may be applied to an $O_2$ sensor without a heater. In this case as well, a condition in which the element temperature decreases (element resistance changes) can be addressed appropriately as mentioned above.

(d) In the above embodiment, determination is made as to whether cold start of the engine 10 or fuel cut is being executed and when it is determined that cold start or fuel cut is being executed, constant current control is performed; instead, however, constant current control may be performed regardless of whether or not cold start or fuel cut is being executed. Namely, S12 in FIG. 8 may be omitted.

(e) For example, when the exhaust gas temperature rises with high load operation of the engine 10 and the element resistance Ra decreases, the sensor applied voltage also changes due to the change in the resistance. In such case, the constant current Ics should be increased.

(f) The structure of the constant current supplying section is not limited to the above constant current circuit 43 but any structure that can supply a prescribed constant current and vary the value of the current may be adopted. For example, a constant current circuit which can adjust the amount of current by PWM control (duty control) may be used. When that is the case, the constant current may be adjusted as a variable according to a current restriction command.

(g) In the above embodiment, the $O_2$ sensor 17 is located downstream of the first catalyst 15a; instead, however, the $O_2$ sensor 17 may be located in the middle portion of the first catalyst 15a. In this case, the $O_2$ sensor 17 may be located on the support of the first catalyst 15a. In any case, the $O_2$ sensor 17 has only to take the exhaust gas purified by the first catalyst 15a as the object of detection and detect the gas components.

(h) The gas sensor is not limited to the above $O_2$ sensor 17, but instead the gas sensor may be a so-called 2-cell gas sensor which includes an electrogenic cell and a pump cell. In this case, the output characteristic of the electrogenic cell of the 2-cell gas sensor can be changed properly and air-fuel ratio determination can be made appropriately.

While the present disclosure has been described with reference to embodiments thereof, it is to be understood that the disclosure is not limited to the embodiments and constructions. The present disclosure is intended to cover various modification and equivalent arrangements. In addition, while the various combinations and configurations, other combinations and configurations, including more, less or only a single element, are also within the spirit and scope of the present disclosure.

The invention claimed is:

1. A gas sensor control device for a gas sensor which has an electromotive cell using a solid electrolyte body and a pair of electrodes placed at a position to interpose the solid electrolyte body, and detects an exhaust gas from an internal combustion engine as an object of a detection and outputs an electromotive force signal depending on an air-fuel ratio of the exhaust gas, the gas sensor control device comprising:
   a constant current supplying circuit configured to supply a constant current that is applied to electromotive cell; and
   a computer comprising a memory storing computer code and a hardware processor for executing the computer code so that the computer is at least configured to perform:
   a calculation of a resistance value of the electromotive cell;
   an air-fuel ratio determination which determines whether the air-fuel ratio is at least rich, lean, or stoichiometric, on the basis of a comparison between an electromotive force output of the electromotive cell and a threshold; and
   a current control which controls the constant current supplied by the constant current supplying circuit, on the basis of the resistance value of the electromotive cell calculated by the resistance value calculation, wherein the current control includes:
      a correction value calculation which calculates a current correction value for the constant current being supplied at a present time point, on the basis of the resistance value of the electromotive cell calculated by the resistance value calculation, and
      a correction which corrects a present constant current that is the constant current at the present time point, by the current correction value.

2. The gas sensor control device according to claim 1, wherein
   the electromotive cell has an output characteristic including a rapid change region where the electromotive force output changes rapidly near a stoichiometric point and a stable region on a richer or leaner side than the rapid change region where the electromotive force output is almost constant, and
   the current control controls the constant current so that the threshold remains included in the rapid change region of the output characteristic.

3. The gas sensor control device according to claim 1, wherein the computer is further configured to perform:

a low temperature determination that determines that a cold start of the internal combustion engine or a fuel cut is being executed, wherein when the low temperature determination determines that the cold start or the fuel cut is being executed, the current control performs a control of the constant current.

4. The gas sensor control device according to claim 1, wherein:

the gas sensor control device for the gas sensor is provided with a heater for heating the electromotive cell, wherein the computer is further configured to perform:

a heater control which controls a drive of the heater so as to control the resistance value of the electromotive cell calculated by the resistance value calculation to be a target resistance value under a condition that the constant current is supplied by the constant current supplying circuit, wherein the current control changes the constant current when the resistance value of the electromotive cell deviates from the target resistance value by a certain amount or more during a heater control performed by the heater control.

5. A gas sensor control device for a gas sensor which has an electromotive cell using a solid electrolyte body and a pair of electrodes placed at a position to interpose the solid electrolyte body, and detects an exhaust gas from an internal combustion engine as an object of a detection and outputs an electromotive force signal depending on an air-fuel ratio of the exhaust gas, the gas sensor control device comprising:

a constant current supplying circuit configured to supply a constant current that is applied to the electromotive cell; and a computer comprising a memory storing computer code and a hardware processor for executing the computer code so that the computer is at least configured to perform:

a calculation of a resistance value of the electromotive cell;

an air-fuel ratio determination which determines whether the air-fuel ratio is at least rich, lean, or stoichiometric, on the basis of a comparison between an electromotive force output of the electromotive cell and a threshold; and a current control which controls the constant current supplied by the constant current supplying circuit, on the basis of the resistance value of the electromotive cell calculated by the resistance value calculation, a constant current setting which sets the constant current supplied by the constant current supplying circuit as a variable, wherein the current control includes a correction value calculation which calculates a current correction value for the present constant current on the basis of a relation between the resistance value of the electromotive cell calculated by the resistance value calculation and the present constant current set by the constant current setting, and a correction which corrects the present constant current by the current correction value.

* * * * *